(12) United States Patent
Bovet et al.

(10) Patent No.: US 9,592,101 B2
(45) Date of Patent: Mar. 14, 2017

(54) RADIO FREQUENCY IDENTIFICATION CAPSULE (RFID)

(71) Applicant: SATYATEK SA, Vevey (CH)

(72) Inventors: Marc Bovet, Develier (CH); Andreas Zielasch, Furstenfeldbruck (DE); Nicolas Gehrig, Chardonne (CH)

(73) Assignee: SATYATEK SA, Vevy (CH)

( * ) Notice: Subject to any disclaimer, the term of this patent is extended or adjusted under 35 U.S.C. 154(b) by 0 days.

(21) Appl. No.: 14/430,641

(22) PCT Filed: Sep. 24, 2013

(86) PCT No.: PCT/IB2013/058815
§ 371 (c)(1),
(2) Date: Mar. 24, 2015

(87) PCT Pub. No.: WO2014/045265
PCT Pub. Date: Mar. 27, 2014

(65) Prior Publication Data
US 2016/0128798 A1   May 12, 2016

(30) Foreign Application Priority Data

Sep. 24, 2012   (WO) .................. PCT/IB2012/055069

(51) Int. Cl.
*A61B 90/98*   (2016.01)
*G06K 19/077*   (2006.01)

(52) U.S. Cl.
CPC .............. *A61B 90/98* (2016.02); *A61B 90/90* (2016.02); *G06K 19/07749* (2013.01); *G06K 19/07754* (2013.01); *G06K 19/07771* (2013.01)

(58) Field of Classification Search
None
See application file for complete search history.

(56) References Cited

U.S. PATENT DOCUMENTS

2004/0220602 A1   11/2004   Deng et al.
2006/0084934 A1*   4/2006   Frank ................. A61F 13/44
                                                  604/362

(Continued)

FOREIGN PATENT DOCUMENTS

CN             102039685      5/2011
DE    20 2011 050941 U1      10/2011

(Continued)

OTHER PUBLICATIONS

International Search Report prepared by the European Patent Office on Feb. 19, 2014, for International Application No. PCT/IB2013/058815.

(Continued)

*Primary Examiner* — Mohamed Barakat
(74) *Attorney, Agent, or Firm* — Sheridan Ross P.C.

(57) ABSTRACT

The invention relates to a radio frequency identification capsule for marking an object. The capsule is characterized in that it comprises: a metal base to be attached to the object; a receiving element for holding a radio tag, the receiving element being secured to the base and overmolded on the base in order to form a durably tight joint with the base; and means for holding the radio tag at a determined distance from the base. The invention allows an automatic inventory of a plurality of marked objects randomly arranged in a highly metal medium and in the presence of Faraday cages.

15 Claims, 9 Drawing Sheets

(56) References Cited

U.S. PATENT DOCUMENTS

| | | |
|---|---|---|
| 2006/0214791 A1 | 9/2006 | Tethrake et al. |
| 2006/0244597 A1 | 11/2006 | Tethrake |
| 2008/0177267 A1 | 7/2008 | Sands et al. |
| 2009/0009332 A1* | 1/2009 | Nunez .............. A01K 11/007 340/572.1 |
| 2009/0266889 A1* | 10/2009 | Turner ............ A61B 17/8685 235/385 |
| 2011/0023343 A1 | 2/2011 | Turner et al. |
| 2012/0020183 A1* | 1/2012 | Loi .................. G06K 19/0675 367/2 |
| 2013/0092564 A1 | 4/2013 | Doherty |
| 2014/0131454 A1 | 5/2014 | Weisshaupt et al. |

FOREIGN PATENT DOCUMENTS

| | | |
|---|---|---|
| DE | 202011050941 | 10/2011 |
| DE | 102011052501 | 2/2013 |
| DE | 102012011922 | 12/2013 |
| EP | 0367629 | 5/1990 |
| EP | 0681252 A1 | 11/1995 |
| EP | 1774917 | 4/2007 |
| EP | 1774917 A | 4/2007 |
| EP | 2082890 | 7/2009 |
| EP | 2634436 | 9/2013 |
| FR | 2899506 | 10/2007 |
| WO | WO 8705487 A | 9/1987 |
| WO | WO 2006/067610 A | 6/2006 |
| WO | WO 2007/090387 A | 8/2007 |
| WO | WO 2009/063323 A2 | 5/2009 |
| WO | WO 2010/109412 A1 | 9/2010 |
| WO | WO 2010/145651 A | 12/2010 |
| WO | WO 2011/054355 A2 | 5/2011 |
| WO | WO 2011/141912 A | 11/2011 |
| WO | WO 2013/020944 A | 2/2013 |

OTHER PUBLICATIONS

Written Opinion prepare by the European Patent Office on Feb. 19, 2014, for International Application No. PCT/IB2013/058815.
Official Action for Canada Patent Application No. 2,886,005, mailed Jun. 5, 2015, 6 pages.
Williams "Polyetheretherketone for Long-Term Implantable Devices," European Medical Device Technology, Jan. 2008, 5 pages [retrieved from: http://www.emdt.co.uk/article/polyetheretherketone-long-term-implantable-devices].

* cited by examiner

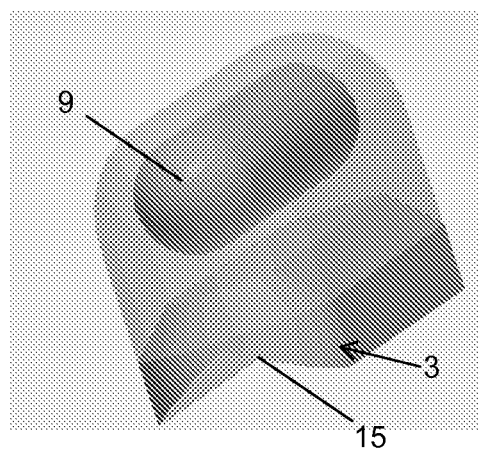
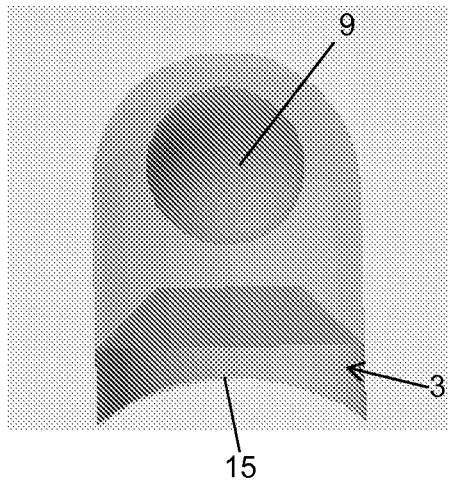
FIG. 5A      FIG. 5B
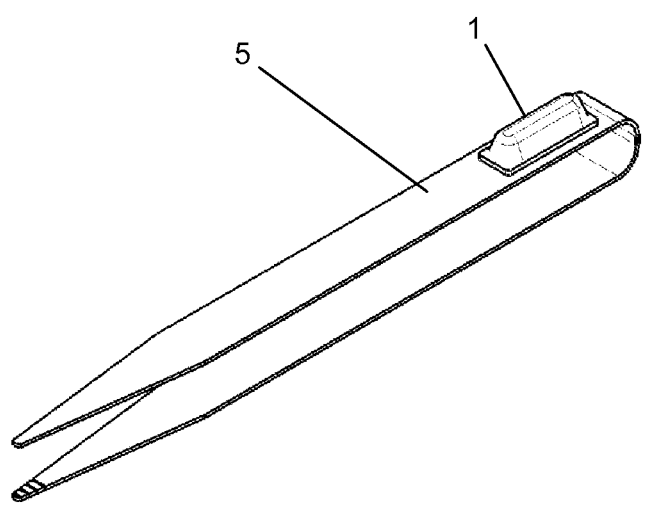
FIG. 6

RADIO FREQUENCY IDENTIFICATION CAPSULE (RFID)

CROSS REFERENCE TO RELATED APPLICATIONS

This application is a national stage application under 35 U.S.C. 371 and claims the benefit of PCT Application No. PCT/IB2013/058815 having an international filing date of Sep. 24, 2013, which designated the United States, which PCT application claimed the benefit of International Application No. PCT/IB2012/055069 filed Sep. 24, 2012, the disclosure of both the above-identified applications are incorporated herein by reference.

The present invention relates generally to a radio-identification (RFID) capsule for the marking of an object and more particularly the RFID marking of reusable medical devices and their bulk, automatic and multiple identification in a strongly metallic environment. The invention applies also to other objects, for example, dental instruments, implants, substitutes of implants, prostheses, tools, industrial, computer-related, railway-related, automotive, nautical and aeronautical components and spare parts and any other similar objects that it is desired to mark in order to ensure its identification and its traceability.

The traceability of the process of retreatment of reusable medical devices makes it possible to guarantee that an instrument has been correctly retreated, that is to say: disinfected, washed, cleaned, dried, checked, packaged, and sterilized before a new use on a patient. The aim of this process is to avoid the transmission of infectious agents to patients.

Instrument-level traceability makes it possible to inform the sterilization agent(s) about the way to treat the instruments (disassembly, immersion, washing, reassembly, verification of functionality, etc.).

Instrument-level traceability also makes it possible to improve the financial and logistical management of instruments (valuation of stock, management of repairs and of the replacement of instruments, materio-vigilance, usage log of the instruments, "dormant" stocks etc.). It also allows inventory checking of a sterilization basket and thus makes it possible to reduce the risks of incidents in the operating room. Indeed, a missing or inappropriate instrument may jeopardize the proper conduct of a surgical operation and represents a risk to the patient's life. An incomplete or incorrect box must be returned for sterilization, thus involving additional work and therefore cost.

Since 2010, the OMS check list "patient safety in the operating room" has required that instruments be counted before and after an operation. The present invention allows the bulk, automatic and simultaneous identification of marked instruments and facilitates the putting of this directive into effect while avoiding human errors and its impact on costs as compared with manual counting by qualified personnel.

Instrument-level traceability makes it possible to control the risk of Creutzfeldt-Jakob Disease (CJD) by identifying the instruments used in patients at risk and thus to block batches of infected instruments.

The individual RFID marking of instruments makes it possible to check at the end of an operation that an instrument has not been forgotten in the body of the patient or thrown into the waste bin together with the operating room dressings.

The invention also makes it possible to prevent the take-up of instruments that are not to be sterilized (single-use instruments or ones that have reached the maximum number of sterilizations).

For reasons of cost (operating time) and safety (reduction, for sterilization agent(s), in the handling of soiled instruments) it is paramount that the instruments can be detected, identified and counted automatically and in bulk in a metal sterilization basket.

Prior Art

Hitherto, several technologies have been used as a partial solution to the above-mentioned problem.

Color Marking

This approach does not make it possible to assign a unique identifier to objects. The system rapidly reaches its limits since it would be necessary to mark each object with a different color, something which is totally impossible. Nonetheless, this solution has the advantage of not requiring any particular apparatus. In the case where a sticker of the same color is applied to all the instruments of a sterilization basket, the color marking has the advantage of allowing fast and manual sorting of the instruments and of helping to sort instruments after their use in the operating room.

Two Solutions Exist:

the use of color rings fastened to the instrument, such as described in patent application WO8705487. This solution exhibits the drawback of creating enclaves of bacteria between the color ring and the instrument, the ring-instrument link not being leaktight;

or the creation of a cavity filled with a polymerizable colored resin, such as described in patent application WO2007090387. This solution has the disadvantage of modifying the instrument and of creating potential breakage points.

Optical Identification, Datamatrix, Micro-Percussion, Etching

Optical codes can be applied to instruments either by etching by means of a laser, or by micro-percussion which consists of a succession of impacts which deform the surface of the part to be marked.

Marking by optical code makes it possible to assign a unique number (GS1-type normalized coding) or an internal number chosen by its owner and therefore to uniquely recognize two objects resembling one another in every respect.

The identification of the instrument thus marked is done by means of a suitable optical reader. The uniqueness of a code is not guaranteed since it is possible to etch a code an infinite number of times. Patent FR2899506 describes a datamatrix coding machine while patent EP0681252A1 describes a scheme for marking a surgical instrument.

Optical marking does not allow automatic, multiple and bulk identification of marked instruments. A dirty, wet or degraded code or any opaque element between the optical code and the reader render reading impossible or difficult. Deep marking of the instrument embrittles it, surface marking disappears easily and must be re-etched often, thus giving rise to very significant expense.

RFID

RFID Technology Makes it Possible:

i) to assign a unique code to each medical device and thus to be able to differentiate in a definite and immediate manner two visually identical objects;

ii) to identify an instrument even if it is packaged, dirty or wet;

iii) to modify without contact with the object all or some of the data contained in the memory of the RFID tag with the exception of its unique code etched during manufacture. This unique code, when it is present, is unfalsifiable. The memory of the tag allows any sort of information, for example a GS1-type normalized coding, to be stored therein.

Various RFID-based marking methods have been fine tuned, the main technical solutions are to:

integrate the RFID tag into a cavity made in the instrument such as described in patents WO2010145651, WO2009063323, WO2006067610, EP1774917.

The first drawback of this solution resides in the fact that it is necessary to machine a cavity in the instrument, thereby embrittling it and presenting a risk of breakage of the instrument during a surgical procedure. Moreover, as surgical instruments are mainly metal, integrating the RFID tag into the material greatly reduces the reading distance. Multiple and bulk identification is therefore no longer possible even in a non-metallic environment.

manufacture a capsule, a button, a fastening which is thereafter fixed onto the instrument to be marked.

Document US20080177267 describes a fastening which is fixed to the instrument. The sealing plane between the fastening and the instrument is not leaktight and offers potential enclaves of bacteria. Furthermore, it is not easy to clean such a part.

Document US20060214791 describes a button tag to be screwed onto the instrument. This solution does not make it possible to obtain an enduringly leaktight sealing plane between the instrument and the button. It is necessary to make a cavity in the instrument so as to be able screw the button thereinto.

Concerning the capsule described in document WO2011141912, the surrounding of the RFID tag by a "C"-shaped metal annulus does not allow bulk, simultaneous and automatic identification of a hundred or so instruments in a surgery basket.

The technology used in document WO2011054355A2 does not allow multiple, automatic and bulk identification in a metallic surgical basket. The RFID capsule is glued by applying a mixture of polymerizable acrylates or methacrylates.

In document WO2013020944, two tags are necessary to allow automatic identification, this being economic nonsense and demonstrating the lack of effectiveness of the RFID technology chosen within the framework of use in a strongly metallic medium. Consequently, multiple, automatic and bulk identification in a metal basket is not possible.

Drawbacks of the Prior Art

To count or check the content of a sterilization basket, it is necessary to identify the instruments one by one, this taking a great deal of time. The prior art does not provide any solution allowing multiple, automatic and bulk identification of marked instruments in a strongly metallic environment, nor any hygienic, versatile marking solution without modifying the instrument (examples of metal sterilization baskets: http://www.aesculap.extranet.bbraun.com/public/frame_doc_index.html?medid=100051310; and
http://www.sterilmed.fr/avec-filliqrane/sterilmed-02-paniers-et-accessoires-2012.pdf).

An aim of the present invention is to address the drawbacks mentioned hereinabove.

More precisely, the aim of the present invention is:

firstly, to propose an RFID capsule for surgical instruments which allows its detection in an automatic manner, in bulk and in a strongly metallic environment in the presence of Faraday cages. Indeed, up to 100 instruments or more may be stored in stainless steel sterilization baskets, their random overlapping and the presence, sometimes, of metal bowls, necessarily create Faraday cages;

secondly, to provide a perfect RFID capsule from a medical and hygienic point of view both in its design and in its assembly;

thirdly, to provide an RFID capsule allowing a fast, permanent, strong and leaktight assembly, without needing to make a cavity in the instrument;

fourthly, to provide an RFID capsule that can be assembled to a great variety of instruments; and fifthly, to provide an RFID capsule that can be fixed to brand new instruments by the manufacturer and also to an already existing instrument pool, meaning that the instruments do not have to be modified in their design to allow their RFID marking.

The present invention thus relates to a radio-identification capsule for the marking of an object, an assembly as claimed in claim 15 and a method of assembling a radio-tag in a radio-identification capsule.

Other advantageous characteristics of the invention are indicated in the dependent claims.

The present invention is composed of a metal plinth overmolded with a composite, the whole integrating a radio-tag (RFID tag) and forming an RFID radio-identification capsule. This RFID capsule can be fixed in a permanent and hygienic manner to a medical device to give it a unique, unfalsifiable and remotely consultable electronic signature.

Other characteristics and advantages of the present invention will be more clearly apparent on reading the detailed description which follows of an embodiment of the invention given by way of wholly non-limiting example and illustrated by the appended drawings, in which.

Figure 1:
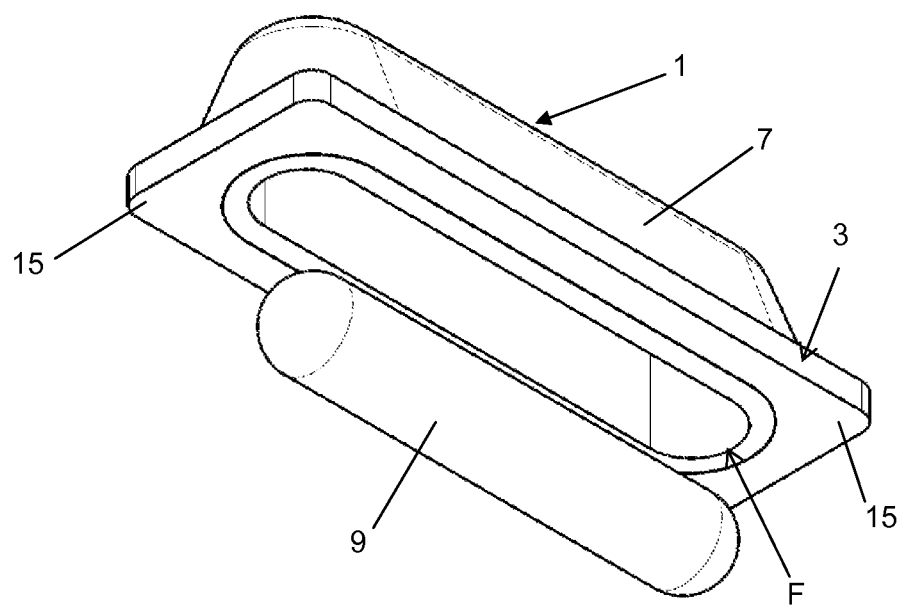
FIG. 1 illustrates an elevational view of a radio-identification capsule according to the present invention.
Figure 3A:
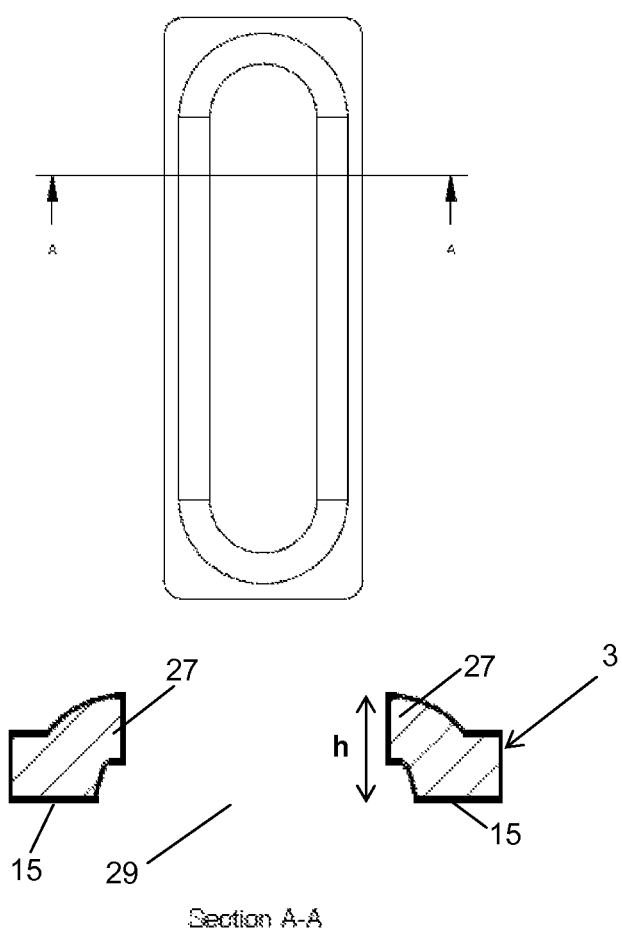
Figure 3B:
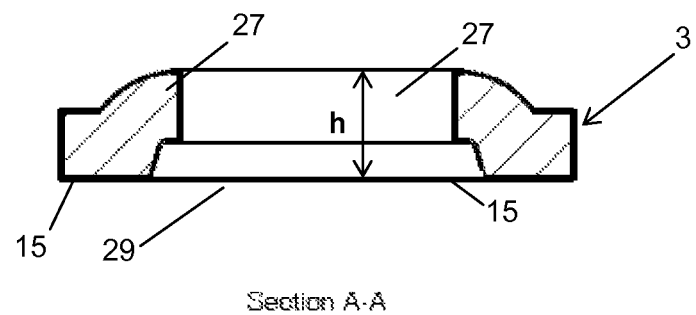
Figure 4:
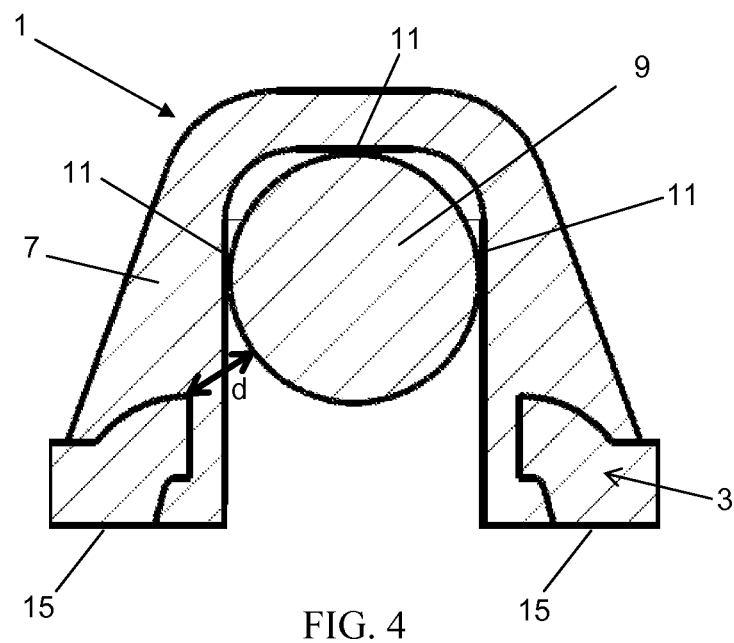
Figure 7:
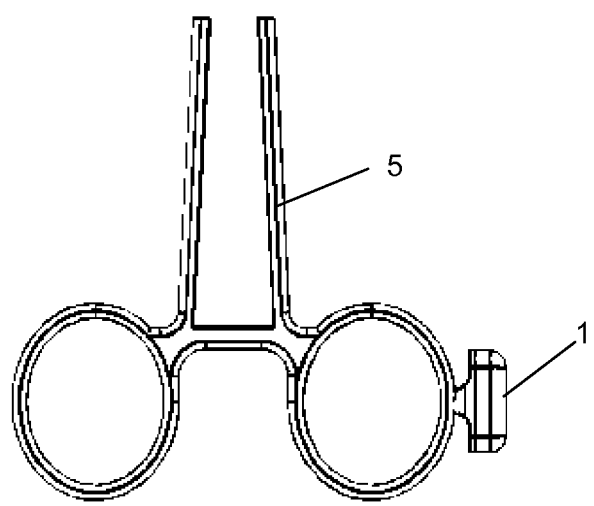
Figure 8:
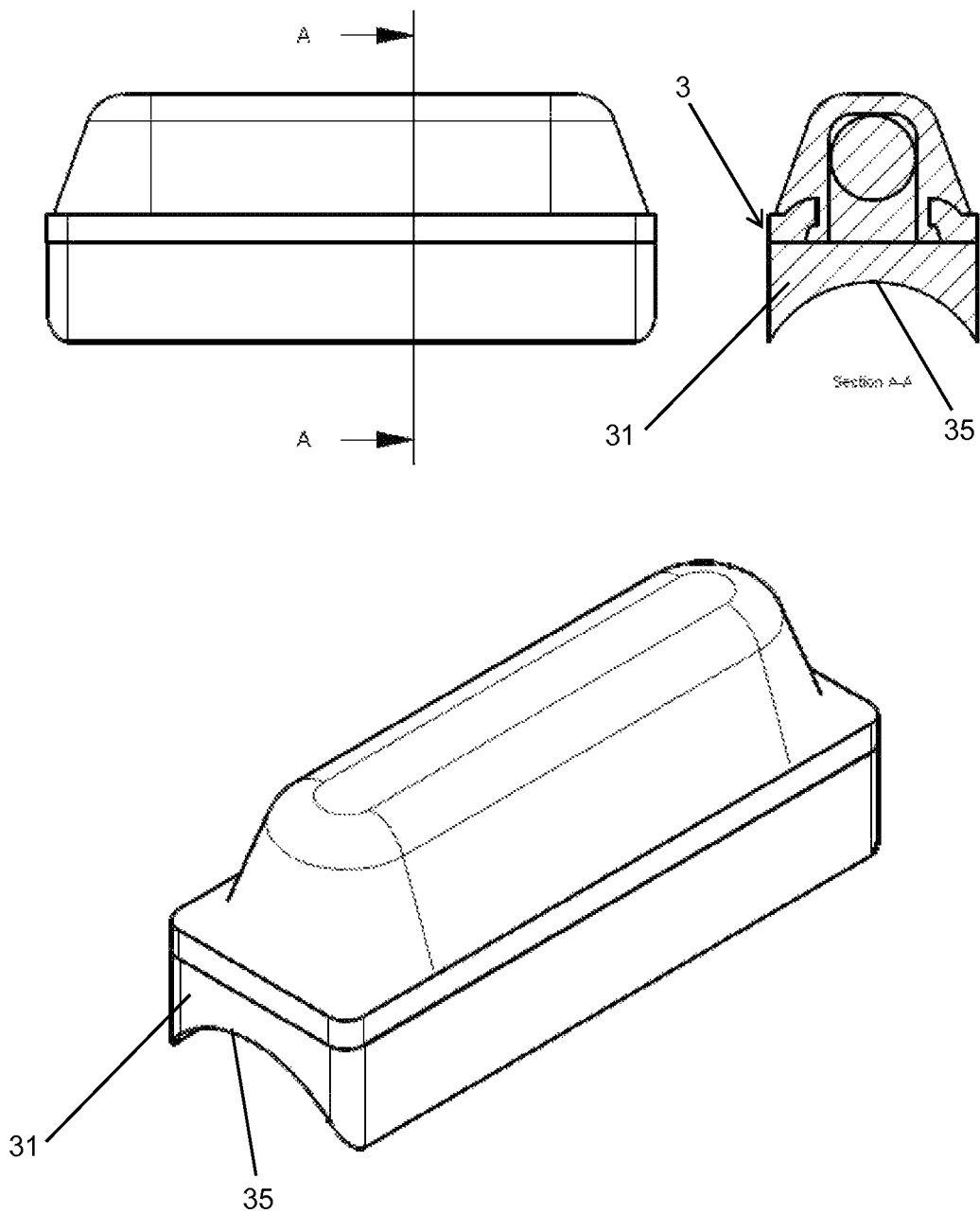
Figure 9:
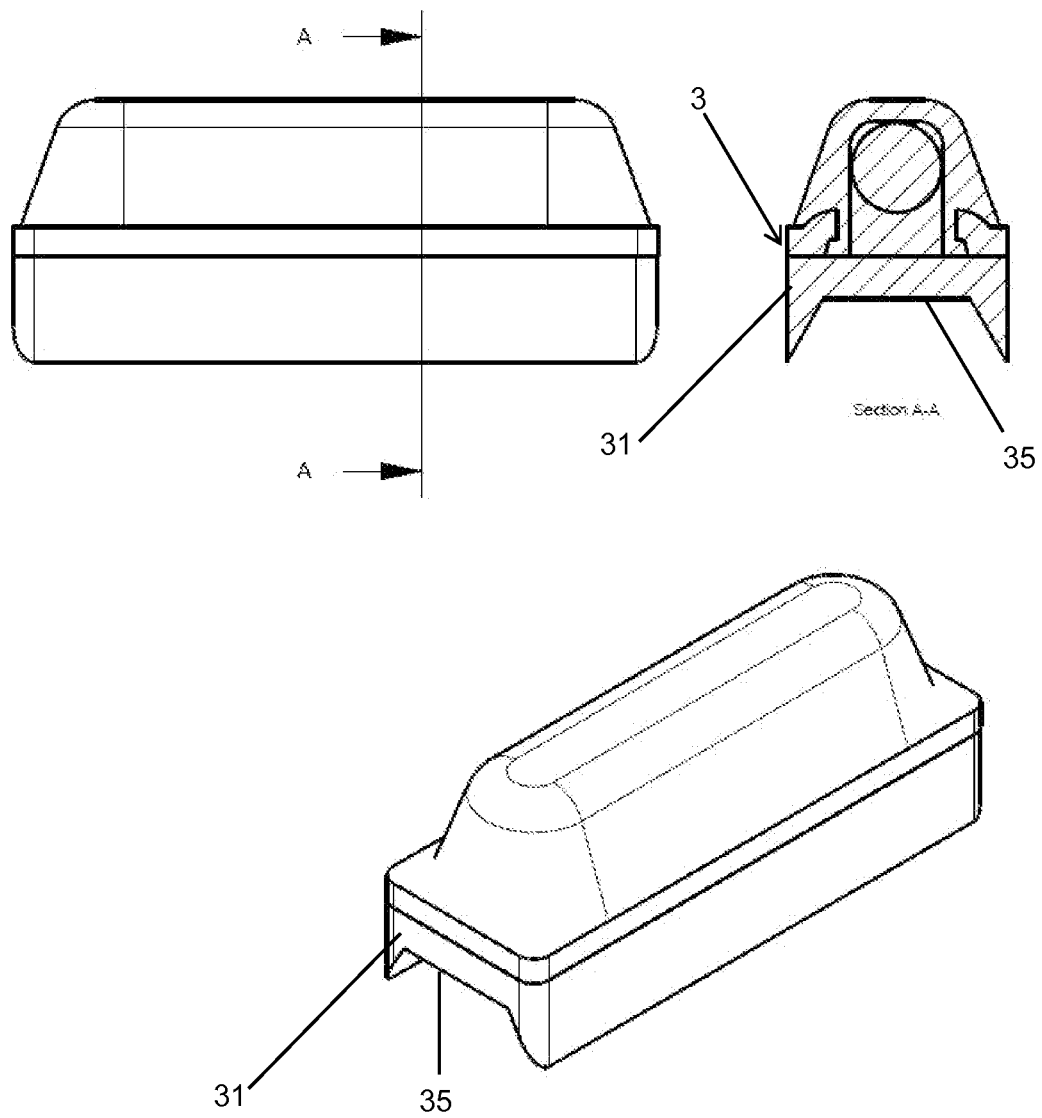
Figure 10:
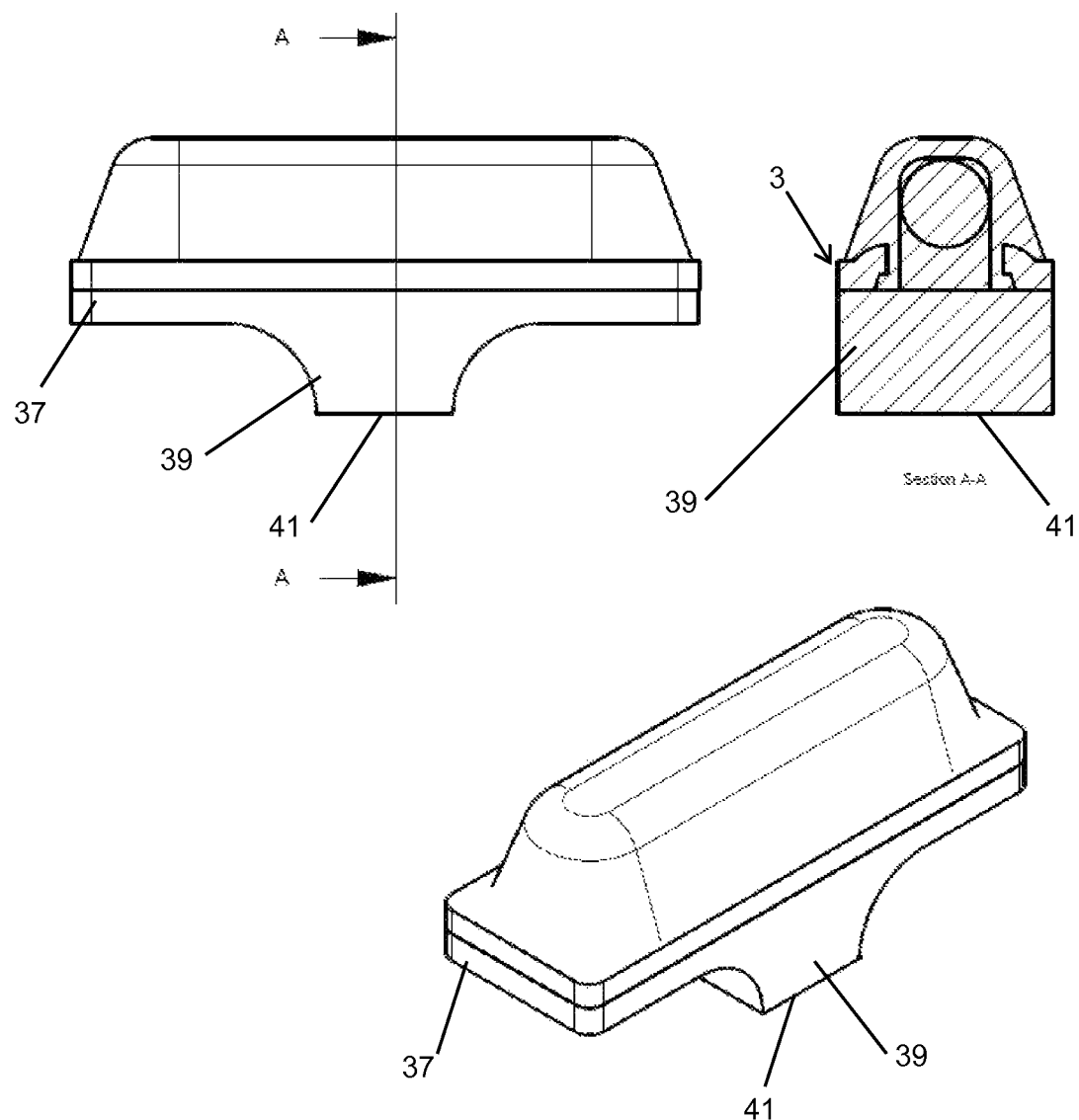
Figure 11:
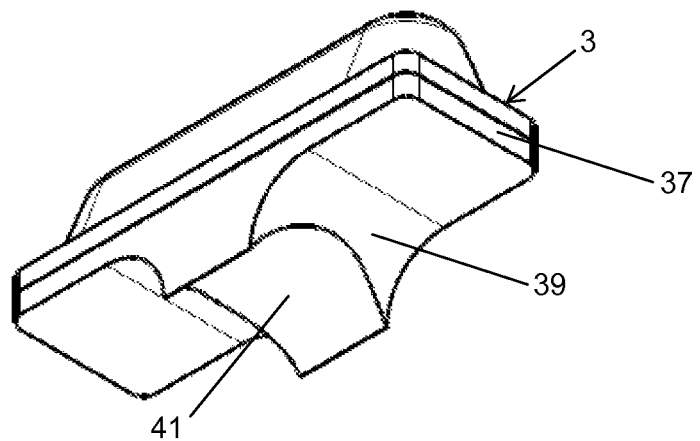
Figure 12:
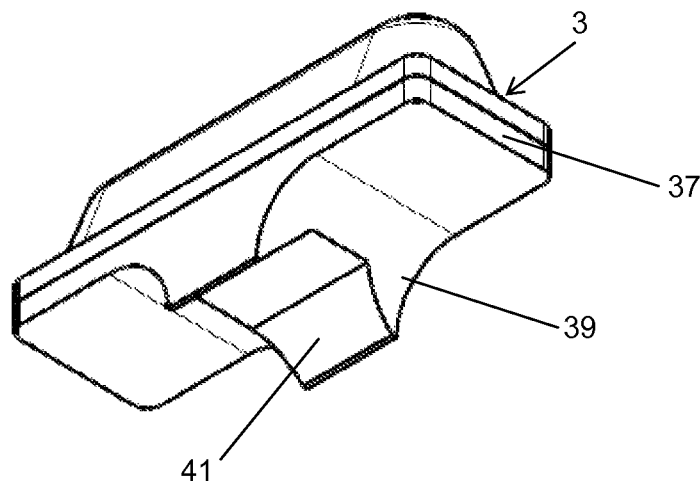

FIG. 3*a* is a sectional view of the radio-identification capsule along the axis A-A;

FIG. 3*b* is a sectional view similar to that of FIG. 3*a* in which the profile of the bottom of the plinth is illustrated (see the reference F of FIG. 1);

FIG. 4 is a sectional view of the radio-identification capsule according to the present invention comprising a radio-tag;

FIG. 5*a* illustrates a plinth of the radio-identification capsule according to the present invention having a chamfer to hug a 6-sided instrument;

FIG. 5*b* illustrates a plinth of the radio-identification capsule according to the present invention having a chamfer to hug a portion of an instrument with a diameter of 6 mm;

FIG. 6 illustrates a radio-identification capsule according to the present invention assembled on a flat surface of an instrument;

FIG. 7 illustrates a radio-identification capsule according to the present invention assembled on a non-flat surface of an instrument;

FIG. 8 shows an elevational view and a sectional view of a radio-identification capsule according to a variant of the present invention comprising a plinth able to hug a round instrument;

FIG. 9 shows an elevational view and a sectional view of a radio-identification capsule according to a variant of the present invention comprising a plinth able to hug a 6-sided instrument;

FIG. 10 shows an elevational view and a sectional view of a radio-identification capsule according to a variant of the present invention comprising a plinth able to hug an instrument on a flat surface;

FIG. 11 is an elevational view of a radio-identification capsule according to a variant of the present invention comprising a plinth able to hug a round instrument; and FIG. 12 is an elevational view of a radio-identification capsule according to another variant of the present invention comprising a plinth able to hug an 8-sided instrument.

Figure 2:
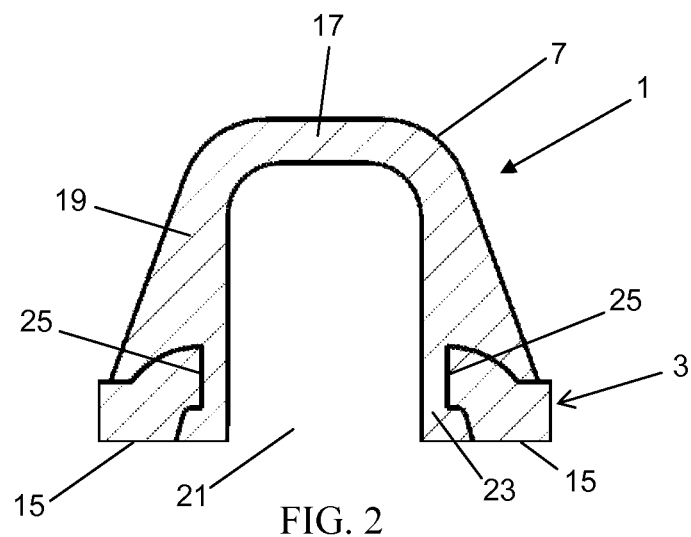
FIG. 2 is a sectional view of the radio-identification capsule according to the present invention.

FIGS. 1 and 2 illustrate a radio-identification capsule 1 (RFID capsule) according to the present invention comprising a metallic plinth (or support) 3 intended to be fixed to an object 5 to be marked (FIGS. 6 and 7) and a housing 7 made preferably of polyetheretherketone (PEEK) able to hold a radio-tag (RFID tag) 9. The housing 7 is secured to the plinth and is overmolded on the plinth 3 to form an enduringly leaktight seal with the plinth 3.

The plinth is, for example, made of stainless steel (316L stainless steel). The housing 7 can be made of polyetheretherketone (PEEK) reinforced with glass fiber or carbon fiber. The polyetheretherketone (PEEK) embodiment can be made in different colors.

The radio-identification capsule 1 furthermore comprises means 11 for holding the radio-tag 9 at a fixed distance d from the plinth 3 (FIG. 4), the distance d being the shortest distance between the plinth 3 and the radio-tag 9.

The means 11 for holding the radio-tag 9 at a fixed distance from the plinth can be clips (claws) present in the housing 7 and fastened to an interior surface of the housing 7 able to receive the radio-tag 9, a gluing of the radio-tag 9 to the interior surface of the housing 7, a filling of the housing with a filling material (for example, a resin or other filling material) or a clipping (for example, by embedding, gluing or welding) of a gripping counter-part (made of a metal composite and in the cavity of the housing) whose shape reproduces in negative the profile of the radio-tag 9.

The housing 7 comprises a bottom 17, a lateral wall 19 linked to the bottom 17 and delimiting an opening 21 for receiving the radio-tag 9 in the housing 9. The housing 7 furthermore includes an edge 23 at the end of the wall 19 including a recess 25. The plinth 3 comprises a setback 27 (FIG. 3) configured to cooperate with the recess 25 making it possible to secure the housing 7 to the plinth 3. The recess 25 allows optimal mechanical binding to the plinth of the encapsulating material of the housing 7.

The plinth 3 has a height h with respect to its exterior surface 15 of at least 0.5 mm (FIG. 3) so that the encapsulating material of the housing 7 is not damaged during the laser welding process. The plinth furthermore includes an opening 29 allowing the insertion of the radio-tag 9 into the housing 7 after overmolding and manufacture of the capsule.

The exterior surface 15 can take various shapes as a function of the geometry of the object to be marked. The exterior surface 15 of the plinth 3 intended to be fixed to an instrument 5 may be flat, curved, endowed with an angle substantially in the middle of the surface of the plinth (FIG. 5A), endowed with a polyhedron or has a substantially circular shape with a predetermined radius (FIG. 5B) so as to properly hug the shape of that portion of the instrument 5 to which the capsule will be fastened.

In the embodiments illustrated in FIGS. 5A, 5B and 8 to 9 and with respect to the plinth 3 of the embodiment illustrated in FIGS. 1 to 4, the plinth 3 furthermore comprises a base 31 closing the housing 7, the base 31 comprising an exterior surface 35 intended to be fixed to an instrument 5. The base 31 is welded to the surface 15 by way of a laser or glued to the surface 15.

This exterior surface 35 may be flat, curved, endowed with an angle substantially in the middle of the exterior surface 35, endowed with a polyhedron or has a substantially circular shape with a predetermined radius (FIG. 8) so as to properly hug the shape of that portion of the instrument 5 to which the capsule will be fastened. FIG. 9 shows a capsule 1 comprising a plinth having an exterior surface 35 able to hug a 6-sided instrument.

In the embodiments illustrated in FIGS. 10 to 12 and with respect to the plinth 3 of the embodiment illustrated in FIGS. 1 to 4, the plinth 3 furthermore comprises a base 37 closing the housing 7 as well as a stud 39 having an exterior surface 41 intended to be fixed to an instrument 5. The base 37 is welded to the surface 15 by way of a laser or glued to the surface 15.

This exterior surface 41 may be flat (FIG. 10), curved, endowed with an angle substantially in the middle of the exterior surface 41, endowed with a polyhedron or has a substantially circular shape with a predetermined radius (FIG. 11) so as to properly hug the shape of that portion of the instrument 5 to which the capsule will be fastened. FIG. 12 shows a capsule 1 comprising a plinth having an exterior surface 41 able to hug an 8-sided instrument.

The housing 7 may be made of plastic, ceramic, silicone, SUS304 silicone, rubber or FKM (about 80% fluoroelastomers). These materials neither block nor reduce the electromagnetic waves and protect the radio-tag 9. The preferred encapsulating material for overmolding the housing 7 on the metal plinth 3 is a PEEK filled with glass fibers or carbon fibers for the following reasons:

Mechanical resistance, especially
  i. Common knocks so as to avoid the breaking of the RFID tag 9
  ii. Resistance to cuts
  iii. Resistance to friction
  iv. To ultrasound baths
Chemical resistance, especially
  i. Caustic soda in molar concentration 1 to 2 exposure
  ii. Ortho-phosphoric acid (for example: Borer Deconex 34)
  iii. Detergents in disinfectant-washes (for example: Borer Deconex 23)
Thermal resistance
  i. At least 1500 cycles in a Prion autoclave (134° C., 18 min, 3 bar of pressure in a distilled water vapor saturated atmosphere),
  ii. Exposure to a temperature of 200°
Biomedical compatibility
  i. Cyto-compatible, and optionally biocompatible, material
  ii. Smooth surface without enclaves of bacteria
  iii. Leaktight sealing plane between the overmolding material and the metal plinth 3
  iv. Durability of leaktightness guaranteed by virtue of the similar thermal expansion coefficients of the metal plinth 3 and of the encapsulating material of the housing 7.
Possibility of coloring the encapsulating substance in various colors The encapsulating material does not terminate at the edge of the metal plinth 3 in order to allow closure of the injection mould during overmolding.

This property also makes it possible to avoid impairment of the encapsulating material when laser welding the RFID capsule 1 to an instrument 5.

The radio-tag (RFID tag) 9 is inserted into the capsule 1 after overmolding.

Within the framework of the use of a low-frequency LF or ultra-high-frequency UHF radio-tag 9 (RFID tags), the fixed distance between the radio-tag 9 and the metal plinth 3 as well as the frequency of the radio-tag 9 make it possible to create a normalized environment as regards the magnetic field. The position of the radio-tag 9 with respect to the plinth 3 is varied and an operating frequency of the radio-tag 9 is determined so as to obtain a position and frequency at which the operating frequency of the capsule 1 is between 121 kHz and 129 kHz (and preferably at 125 kHz). It is thus possible to specify and guarantee optimal RFID performance (reading distance and reliability) as a function of the substance of the object to which the RFID capsule 1 will be fixed.

If an LF radio-tag 9 is used, it should be noted that the distance d between the radio-tag 9 and the metal plinth 3 must be fixed by the means 11 at a value of about 0.2 mm, for example. The resonant frequency of the radio-tag 9 is adapted to suit the metal used so that once in the presence of the metallic plinth 3, the capsule 1 operates at a normalized value between 121 kHz and 129 kHz (and preferably about 125 kHz (or at 125 kHz)) before assembling the capsule 1 to the object 5 and when the capsule is assembled on the object 5 to be marked.

Indeed, if a radio-tag 9 is applied directly to a metallic surface, the diverse detuning effects would render detection of the radio-tag 9 either impossible or the detection distance would be too slight to allow bulk and automatic identification in a metallic sterilization basket. The "normalization" strategy hereinabove makes it possible to automate the detection of objects marked by the RFID capsule 1 and to preserve instantaneous and automatic detection of objects placed in bulk in a sterilization basket which is placed in an RFID tunnel such as described in the patent application: P2012PC00—SYSTEME ET PROCEDE POUR LA LECTURE D'UN OU DE PLUSIEURS TAGS RFID EN MODE ANTICOLLISION DANS UNE CASSETTE METALLIQUE ET EN DEHORS [SYSTEM AND METHOD FOR READING ONE OR MORE RFID TAGS IN ANTICOLLISION MODE IN A METALLIC CASSETTE AND OUTSIDE].

Preferably, passive radio-tags 9 operating at low frequency 35-150 kHz are used.

Preferably, the radio-tag 9 takes the form of a cylindrical object comprising:

An RFID transponder or chip

A ferrite (of cylindrical, E, U or curved shape)

A copper coil welded to the transponder and optionally a glass tube protecting the elements hereinabove.

These radio-tags 9 are usually called "glasstags" or "metal rod tags" and exist in various dimensions and forms. They may also be equipped with various types of transponders especially at low (LF) or high frequency (HF). They are marketed in particular by the company HID Global under this label (see the link: http://www.hidglobal.com/documents/hid-rfid-il-glass-tag-family-ds-en.pdf)

The present invention also makes it possible to adapt to suit UHF radio-tags of small dimensions, such as those proposed by the company Xerafy. They are marketed in particular under the label Dot-On XS and Dash-On XS.

Radio-tags equipped with an air coil may also be used, these radio-tags generally take the form of disks. They are marketed in particular by the company HID Global under the trade name MicroProx™ tag, (see the link: http://www.hidglobal.com/main/id-cards/hid-proximity/1391-microprox-tag.html).

For other objects to be equipped of larger size than instruments or tools, for example containers, trolley or palettes, RFID radio-tags of other shapes and operating with other frequencies (HF, UHF, MW) may be used. They are marketed in particular by the company HID Global under the trade name InLine UHF™ tag (see the link http://www.hidglobal.com/documents/hid-inline-230-15-uhf-tag-ds.en.pdf).

The RFID radio-tags used (LF glasstags) withstand more than 1500 Prion sterilization cycles and they withstand ultrasound baths.

The microchip used in the radio-tag 9 possesses an anti-collision algorithm to identify one by one the objects of a collection of objects during multiple readings.

The fact that all or some of the object to be marked is made of metal does not prevent an object from being identified among the collection of objects.

The presence of metal does not prevent the automatic detection of objects among a collection of objects.

The objects marked by means of the capsule of the present invention can be deposited in a stainless steel sterilization basket, a surgical tray, in a closed metallic cassette, a "kidney dish", a sterilization basket and it is always possible to detect the objects among the collection of objects.

It will be understood that diverse modifications and/or improvements obvious to the person skilled in the art may be made to the various embodiments of the invention that are described in the present description without departing from the scope of the invention, as defined by the appended claims.

The invention claimed is:

1. A radio-identification capsule for the marking of an object, the capsule comprising:
    a metallic plinth configured to be fixed to the object;
    a pre-existing housing with a cavity to receive and hold a radio-tag to be inserted into the housing cavity, the housing being secured to the plinth and overmolded on the plinth so as to form an enduringly leaktight seal with the plinth;
    means for holding the radio-tag at a fixed distance from the plinth,
    the capsule being characterized in that the housing is made of polyetheretherketone (PEEK) reinforced with carbon or glass fiber.

2. The radio-identification capsule as claimed in claim 1, wherein the plinth has a height of at least 0.5 mm.

3. The radio-identification capsule as claimed in claim 1, wherein the housing includes an opening for inserting a radio-tag, and/or in that the plinth includes an opening for inserting a radio-tag into the housing cavity.

4. The radio-identification capsule as claimed in claim 1, wherein the plinth is made of stainless steel.

5. The radio-identification capsule as claimed in claim 1, wherein the housing comprises a single radio-tag and the capsule is configured to operate at about 125 kHz when the capsule is assembled on the object thus forming a normalized environment allowing the detection of the object in a metal sterilization basket.

6. The radio-identification capsule as claimed in claim 1, wherein the housing comprises a bottom, a lateral wall linked to the bottom delimiting an opening for receiving a radio-tag in the housing cavity, an edge at the end of the wall including a recess; and in that the plinth includes a setback able to cooperate with the recess so as to secure the housing to the plinth.

7. The radio-identification capsule as claimed in claim 1, wherein the plinth comprises a base closing the housing and comprising an exterior surface configured to be fixed to the object.

8. The radio-identification capsule as claimed in claim 6, wherein the plinth comprises a base closing the housing as well as a stud comprising an exterior surface configured to be fixed to the object.

9. The radio-identification capsule as claimed in claim 1, wherein an exterior surface of the plinth configured to be fixed to the object is flat, curved, endowed with an angle substantially in the middle of the surface of the plinth, endowed with a polyhedron or has a substantially circular shape of a radius predetermined so as to properly hug the shape of the object to be marked.

10. The radio-identification capsule as claimed in claim 1, wherein the housing is able to be produced in different colors.

11. The radio-identification capsule as claimed in claim 1, wherein the means for holding the radio-tag at a fixed distance from the plinth comprise clips present in the housing cavity, a gluing of the radio-tag in the housing cavity, a filling of the housing by a filling material or a clipping of a counter-part in the housing cavity.

12. The radio-identification capsule as claimed in claim 1, wherein the radio-tag is maintained at a distance of about 0.2 mm from the plinth.

13. An assembly comprising an object and the capsule as claimed in claim 1, wherein the plinth of the capsule being welded to the object by way of a laser or glued on the object.

14. The assembly as claimed in claim 13, in which the object is a medical, surgical or dental instrument, or a tool, a railway-related, automotive, nautical or aeronautical part or spare part.

15. A method of assembling a radio-tag in a radio-identification capsule as claimed in claim 1, so as to provide a radio-identification capsule operating between 121 kHz and 129 kHz when the capsule is assembled on an object and to form a normalized environment allowing the detection of the object in a metal sterilization basket comprising a plurality of objects, the method comprising the steps of:
inserting a radio-tag into the housing of the capsule;
varying the position of the radio-tag with respect to the plinth and defining its operating frequency so as to determine a position and frequency at which the operating frequency of the capsule is between 121 kHz and 129 kHz; and
fixing the radio-tag at this determined position by using the means for holding the radio-tag at a fixed distance from the plinth.

* * * * *